United States Patent [19]

Jacobs et al.

[11] Patent Number: 5,443,480
[45] Date of Patent: * Aug. 22, 1995

[54] SHARPLY ANGLED KELLY (JACOBS) CLAMP

[75] Inventors: Moises Jacobs, Miami; Charles R. Slater, Fort Lauderdale; Kevin W. Smith, Miami, all of Fla.

[73] Assignee: Symbiosis Corporation, Miami, Fla.

[ * ] Notice: The portion of the term of this patent subsequent to Jun. 1, 2010 has been disclaimed.

[21] Appl. No.: 49,633

[22] Filed: Apr. 19, 1993

Related U.S. Application Data

[63] Continuation of Ser. No. 780,035, Oct. 21, 1991, Pat. No. 5,215,101, which is a continuation-in-part of Ser. No. 521,766, May 10, 1990, Pat. No. 5,133,727, and a continuation-in-part of Ser. No. 680,392, Apr. 4, 1991, Pat. No. 5,192,298.

[51] Int. Cl.$^6$ .............................................. A61B 17/28
[52] U.S. Cl. .................................................... 606/207
[58] Field of Search .............................. 128/749, 751; 606/205–208, 170, 171, 174, 142, 190

[56] References Cited

U.S. PATENT DOCUMENTS

| | | |
|---|---|---|
| 3,404,677 | 10/1968 | Springer . |
| 3,446,211 | 5/1969 | Markham . |
| 3,964,468 | 6/1976 | Schulz . |
| 4,950,273 | 8/1990 | Briggs .................... 606/174 X |
| 5,201,753 | 4/1993 | Brown et al. ................ 128/751 X |
| 5,251,101 | 6/1993 | Jacobs et al. ................ 606/207 X |

FOREIGN PATENT DOCUMENTS

| | | | |
|---|---|---|---|
| 0207829 | 1/1987 | European Pat. Off. ..... | A61B 10/00 |
| 2506471 | 8/1975 | Germany .................. | A61B 17/28 |
| WO83/00992 | 3/1983 | WIPO ....................... | A61B 1/06 |

OTHER PUBLICATIONS

Zucker et al., "Surgical Laparoscopy", 1991, p. 49.
Mueller, "The Surgical Armamentarium", 1980, see entire document.
Dräger, "Instrumentekunde", 20 Nov. 1990, Theime Verlag, pp. 98–103.

*Primary Examiner*—Lee S. Cohen
*Assistant Examiner*—Samuel Gilbert
*Attorney, Agent, or Firm*—David P. Gordon

[57] ABSTRACT

A Jacobs type curved clamping or dissector element for a disposable laparoscopic instrument is provided. The Jacobs' type end effectors generally comprises first and second pivotally mounted elongate, opposed clamp members each of which has a straight base portion, an intermediate portion extending away from the axis of the base portion and a curved distal portion which angles 70 to 90 degrees relative to the intermediate portion and which extends back toward and slightly beyond the longitudinal projection of the base portion. The clamp members note when pivotally rotated to a closed-clamp position.

15 Claims, 3 Drawing Sheets

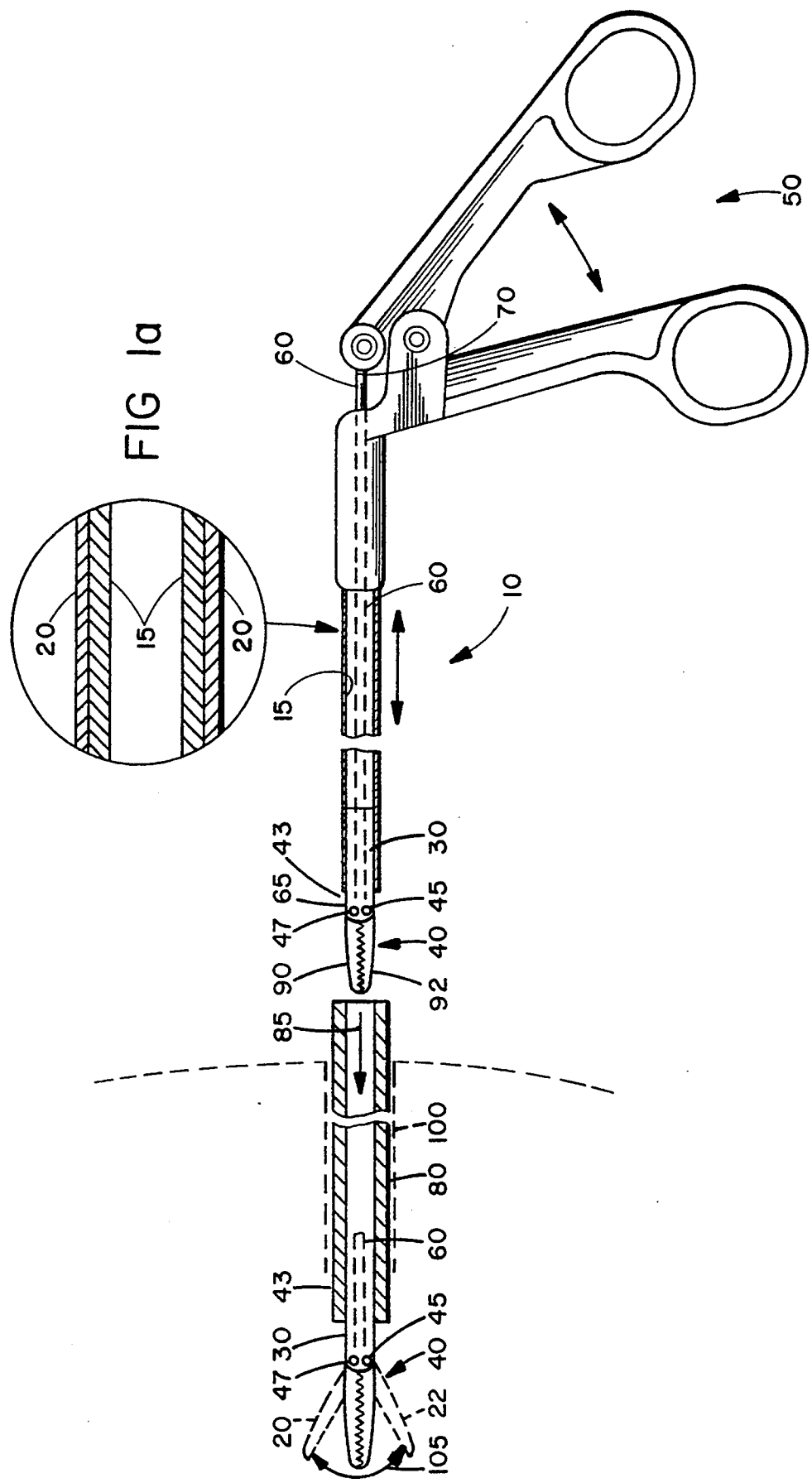

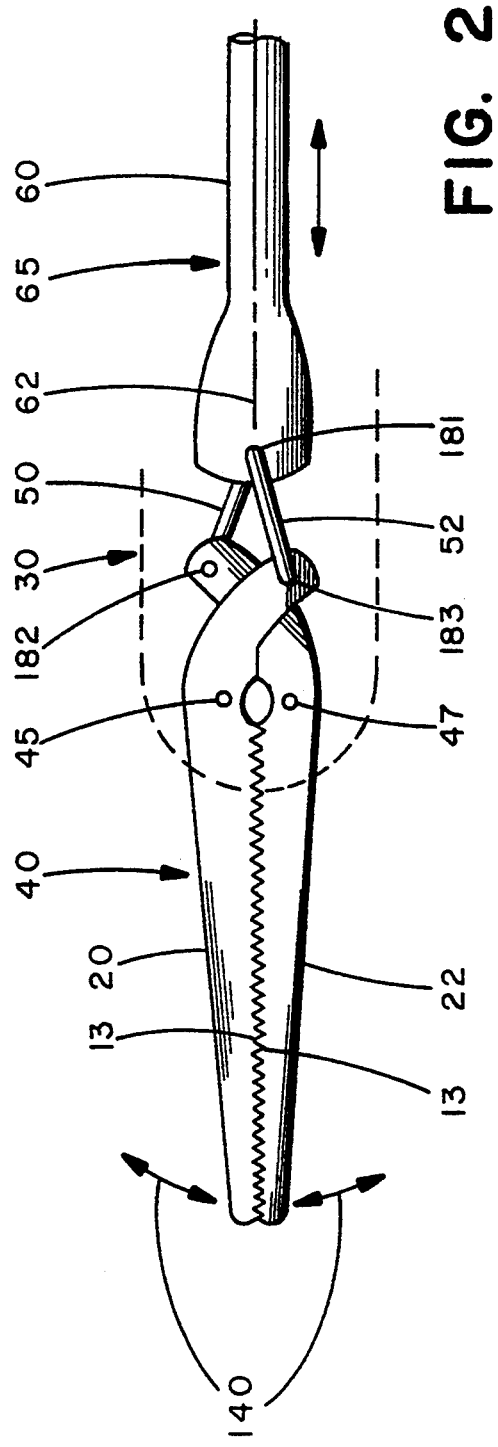
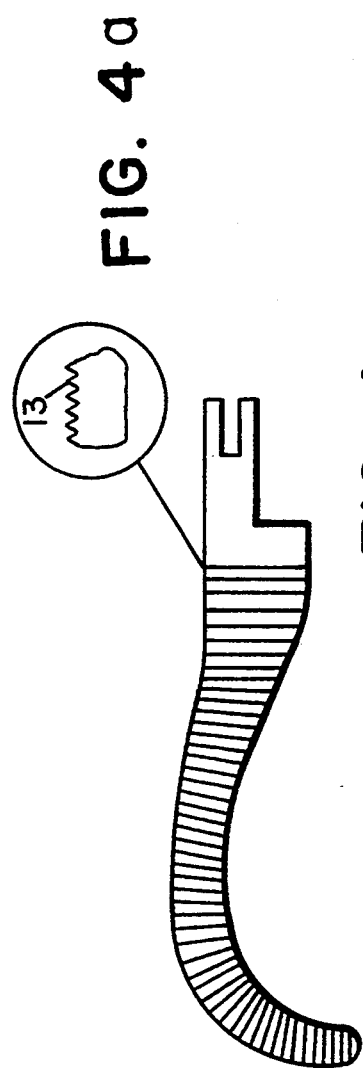

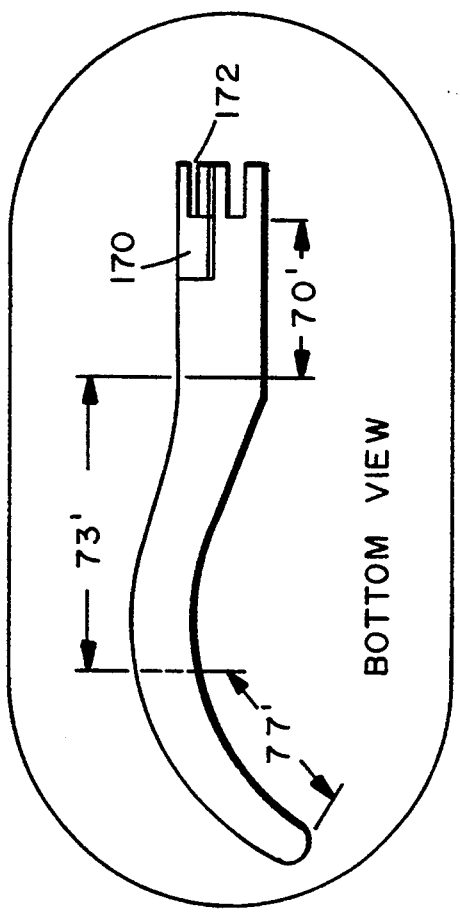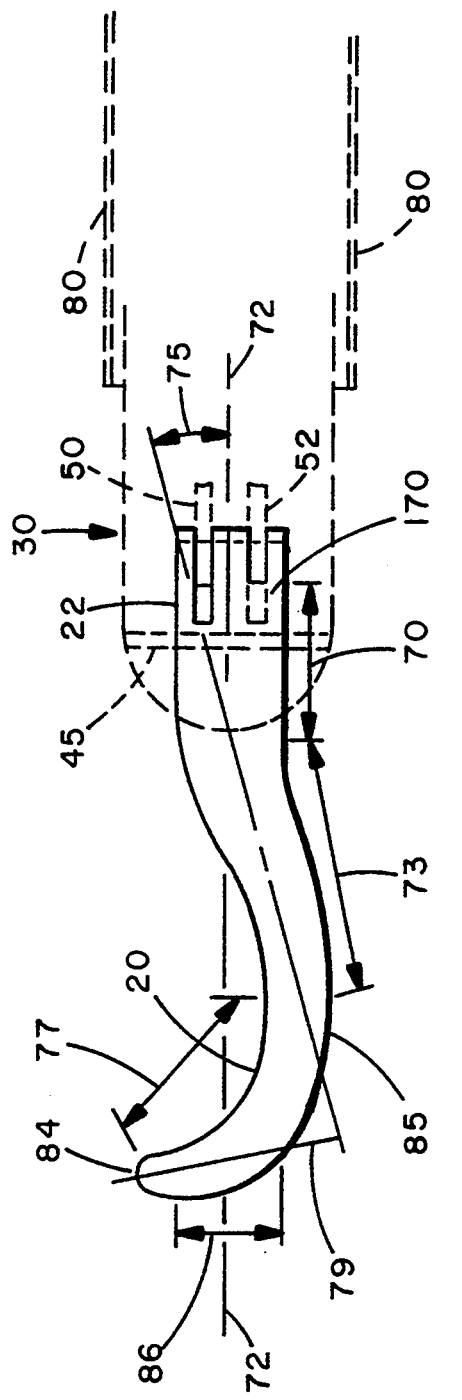

SHARPLY ANGLED KELLY (JACOBS) CLAMP

This is a continuation of application, Ser. No. 07/780,035, filed Oct. 21, 1991, now U.S. Pat. No. 5,215,101, which in turn is a continuation-in-part of application Ser. No. 07/521,766, filed May 10, 1990, now U.S. Pat. No. 5,133,727, and a continuation-in-part of application 07/680,392, filed Apr. 4, 1991, now U.S. Pat. No. 5,192,298.

This application also relates to U.S. Ser. No. 07/780,014 now U.S. Pat. No. 5,171,258, which is also incorporated by reference herein.

BACKGROUND OF THE INVENTION

The present invention broadly relates to laparoscopic surgical instruments. More particularly, the invention relates to disposable laparoscopic clamps useful in a laparoscopy procedure which involves spreading, separating and dividing tissue (i.e., dissection).

The laparoscopy procedure has recently become a widely practiced surgical procedure. A laparoscopy procedure typically involves incising through the navel and through the abdominal wall for viewing and/or operating on the ovaries, uterus, gall bladder, bowels, appendix, although more recently, incisions and insertion of trocar tubes have been made in different areas of the abdomen and even in the chest cavity. Typically, trocars are utilized for creating the incisions. Trocar tubes are left in place in the abdominal wall so that laparoscopic surgical tools may be inserted through the tube. A camera or magnifying lens is often inserted through the largest diameter trocar tube (e.g. 10 mm diameter) which is generally located at the navel incision, while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

Previous to the present invention, laparoscopic tools have utilized curved Kelly type clamps with dissectors having a curved distal portion which was necessarily of limited transverse length (i.e., the length perpendicular to the longitudinal axis of the trocar tube) to permit its passage through a trocar tube. However, because of the limited transverse length of the dissector members, laparoscopic Kelly type clamps have found limited applicability, as they cannot readily reach otherwise inaccessible areas for dissection and/or clamping.

SUMMARY OF THE INVENTION

It is therefore an object of the invention to provide a laparoscopic surgical instrument which dissector elements which traverse a relatively large transverse distance.

Another object of the invention is to provide disposable laparoscopic surgical instruments having high leverage dissector elements.

It is a further object of the invention to provide a disposable laparoscopic surgical instrument with dissector elements which angle sharply relative to the longitudinal axis of the instrument.

In accord with the objects of the invention, a "Jacobs" type curved clamping or dissector element for a disposable laparoscopic instrument is provided. The Jacobs type end effector generally comprises first and second pivotally mounted elongate, opposed clamp members each of which has a straight base portion, an intermediate portion extending away from the axis of the base portion and a curved distal portion which angles 70 to 90 degrees relative to the intermediate portion and which extends back toward and slightly beyond the longitudinal projection of the base portion. The clamp members pivot to achieve a mutually in-register position when pivotally rotated to a closed-clamp position.

A better understanding of the disposable laparoscopic Jacobs' clamp surgical instrument of the invention, and additional advantages and objects of the invention will become apparent to those skilled in the art upon reference to the detailed description and accompanying drawings.

BRIEF DESCRIPTION OF THE DRAWINGS

FIG. 1 is a side elevation view, partly in section, of a disposable laparoscopic instrument prior to insertion into a trocar tube, and, in partial phantom format, after insertion into a trocar tube;

FIG. 1a is a cross section through FIG. 1 at the indicated location of FIG. 1;

FIG. 2 is a side elevation view of the Jacobs type end effector clamps of the invention;

FIG. 3 and 3a are respectively a top plan view and a bottom plan view of the Jacobs type clamp device of FIG. 2 with clamps hooking right and left respectively; and FIG. 4 is a top plan view of a single clamping member of the device of FIG. 2 with clamp hooking left.

DETAILED DESCRIPTION OF THE PREFERRED EMBODIMENT

With reference to FIG. 1 and 1a, a disposable laparoscopic surgical instrument is indicated at 10. The disposable laparoscopic surgical instrument 10 includes an aluminum tube 15 surrounded by a peripheral insulating shrink wrap layer of plastic 20, a clevis means 30, Jacobs type end effector 40, actuating means 50, and a push rod 60. The clevis means 30 is preferably a separately formed aluminum piece which fixedly engages aluminum tube 15. The clevis 30 also engages the Jacobs' clamp manipulating members 20, 22 of the end effector 40. Members 20, 22 are pivotally engaged to clevis 30 at pivot pins 45, 47 as more particularly described in previously incorporated Ser. No. 07/780,014. End effector 40 is preferably formed of investment cast bronze. Alternately, end effector 40 can be formed of investment cast stainless steel, or other metal as desired. The push rod 60, which is preferably formed of stainless steel, is engaged at its distal end 65 to the end effector 40, as hereinafter more fully described, and is connected at 70, at its proximal end, to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the manipulating members 20, 22 of the end effector 40, in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, the manipulating members 20, 22 can be opened and closed as indicated at 105 by reciprocal motion of push rod 60 which results from operation of the manual actuating means 50. The clevis effectively translates the reciprocal motion of the push rod 60 into the end effector means action indicated at 105.

With reference to FIG. 2, a curved clamping end effectors of the Jacobs type (an improved Kelly clamp) in accordance with the present invention is shown at 40 having first and second clamp members 20, 22 pivotally mounted to a clevis 30 at transverse pivot pins 45, 47 to enable and opening and closing clamp motion as indicated at 140 upon actuation of push rod 60. The clamp members 20, 22 are preferably provided with horizontal gripping grooves 13 on their gripping sides (see FIG. 4), with the grooves angling in a manner to be transverse the longitudinal axis of each portion of the clamp member as the clamp member curves. The flattened extension 62 of push rod 60 is coupled to clamp members 20, 22 by metal connectors 50, 52 which engage cutouts 172 in the end portions 170 of the clamp members 20, 22. The metal connectors 50, 52 are attached to the flattened extension 62 by pin 181 (seen in FIG. 2) and are held into the cutouts 172 by pins 182 and 183 (seen in FIG. 2). The opening and closing of clamp 40 is accomplished in the same manner as disclosed in previously incorporated Ser. No. 07/780,014, and details may be obtained by reference to the same.

As may be seen with reference to FIG. 3 and 3a, clamp members 20 and 22 are mirror images of each other, except that the rear portions 170 of the base portions 70 which receive the link members (connectors) 50, 52 are identical rather than being mirror images. The change at the rear portion 170 of the base portion permits the link members to extend past each other and helps provide the high leverage dual pivot arrangement explained in detail in previously incorporated Ser. No. 07/780,014.

As seen in FIGS. 3, 3a, and 4, each of the opposed elongate clamp members has a longitudinally extending substantially straight base portion 70, 70' which is in-line with the axis 72 of push rod 60, an integral substantially straight middle portion 73, 73' which extends away from the axis 72 of the base portion 70 at an angle of about 5° to 20° indicated at 75, and a curved terminal portion 77, 77' which extends back toward the axis 72 of the base portion 70 at an angle of between about 70° and 90° indicated at 79. The end 84 of curved terminal portion 77, and the tangential end 85 of intermediate portion 73 each extend beyond the longitudinal projection 86 of base portion 70. However, both of these locations are within the longitudinal envelope of trocar tube 80 through which the Jacobs' clamp tool is inserted.

Typical dimensions for a Jacobs' type clamp in accordance with the present invention are:
length of base portion: 0.30 inches
length of intermediate portion: 1.00 inches
length of distal portion: 0.40 inches
Angle "72": 5 degrees
Angle "79": 75 degrees
Width of base portion "70": 0.18 inches
Width of intermediate portion "73": 0.13 inches
Width of terminal portion "77": 0.12 inches The configuration of the Jacobs' type clamp as above-described provides a curved terminal portion which traverses a distance transverse the longitudinal axis of the tool which is approximately equal to the diameter of the trocar tube through the tool is passed. Thus, for a ten millimeter trocar tube, the transverse distance is about ten millimeters. The increased length of the curved terminal portion increases the usefulness of the clamp in the dissection of ducts and arteries.

There has been described and illustrated herein a laparoscopic Jacobs type clamp. While particular embodiments of the invention have been described, it is not intended that the invention be limited exactly thereto, as it is intended that the invention be as broad in scope as the art will permit. Thus, while a particular tool arrangement was disclosed, it will be appreciated that the Jacobs type clamp end effectors can be used with different types of instruments. Similarly, while the opening and closing of the clamps was described as being accomplished through the use of a high leverage dual pivot arrangement, a single pivot arrangement such as is disclosed in U.S. Ser. No. 07/680,392 can be utilized. Further, while preferred lengths, widths, and angles for the end effector clamps were described, it will be appreciated that other dimensions can be utilized, provided, of course, that the middle portion curve away from the longitudinal axis of the tool, and that the distal (terminal) portion curve back at a relatively large angle (e.g., approximately 70-90 degrees). In this manner a relatively sharp sweep for the end effectors is provided which extends almost the full diameter of the trocar tube. Therefore, it will be apparent to those skilled in the art that other changes and modifications may be made to the invention as described in the specification without departing from the spirit and scope of the invention.

What is claimed is:

1. In a surgical instrument adapted for insertion through a trocar tube and having a hollow tube with distal and proximal ends and a first longitudinal axis, a clevis coupled to the distal end of said hollow tube, first and second pivot pins, first and second elongate opposed clamp members each having a proximal base portion having a first through-hole for pivotally engaging said clevis with a respective one of said first and second pivot pins, and an actuation means extending through said hollow tube and coupled to said base portion of said first and second clamp members for effecting pivotal rotation of said clamp members, an improvement in said first and second clamp members comprising:

a) each said clamp member further including an intermediate portion and a distal portion integral with said base portion, said intermediate portion and said distal portion of said second clamp member being substantially a mirror image of said intermediate portion and said distal portion of said first clamp member, each said base portion having a second longitudinal axis substantially parallel said first longitudinal axis, each said intermediate portion angling away from said second longitudinal axis of said base portion at an angle of between about 5 to 20 degrees, and each said distal portion angling back toward and past said first longitudinal axis at an angle of between about 70 to 90 degrees relative thereto, wherein at least a portion of said intermediate portion extends along a horizontal axis perpendicular to said first longitudinal axis beyond a longitudinal projection of said base portion in a first direction, and at least a portion of said distal portion extends along said horizontal axis beyond the longitudinal projection of said base portion in a second direction opposite said first direction.

2. The improvement according to claim 1, wherein:
each said clamp member is an integral curvalinear element.

3. The improvement according to claim 2, wherein:
each said clamp member traverses a distance of approximately 10 millimeters along said horizontal axis.

4. The improvement according to claim 1, wherein:
each said clamp member has a clamping surface, and each clamping surface has grooves, wherein the grooves of said distal portions are at an angle of between about 0 to 20 degrees relative to said first longitudinal axis, and wherein the grooves of said intermediate portions are at an angle of between 70 to 90 degrees relative to said first longitudinal axis.

5. The improvement according to claim 4, wherein:
each said clamp member is an integral curvalinear element, and
said base portions and said distal portions each have lengths which are about 0.25 to 0.5 the length of said intermediate portions.

6. The improvement according to claim 5, wherein:
said actuation means in said surgical instrument comprises a push rod extending through said hollow tube and connecting means for connecting said push rod to said base portions of said first and second clamp members, said connecting means being coupled to said push rod and to said base portions of said first and second clamp members, and
each said base portion includes means for coupling to said connecting means.

7. The improvement according to claim 1, wherein:
said base portions and said distal portions each have lengths which are about 0.25 to 0.5 the length of said intermediate portions.

8. The improvement according to claim 1, wherein:
said actuation means in said surgical instrument comprises a push rod extending through said hollow tube and connecting means for connecting said push rod to said base portions of said first and second clamp members, said connecting means being coupled to said push rod and to said base portions of said first and second clamp members, and
each said base portion includes means for coupling to said connecting means.

9. An endoscopic Jacobs type curved clamp apparatus, comprising:
a) a hollow tube having a first end, a second end, and a longitudinal axis;
b) a clevis mechanically coupled to said first end of said hollow tube;
c) first and second pivot pins;
d) first and second elongate opposed clamp members, each clamp member having a proximal base portion, an integral intermediate portion, and an integral distal portion, said intermediate portion and distal portion of said second clamp member being substantially a mirror image of said intermediate portion and distal portion of said first clamp member,
each said base portion having a first through-hole pivotally engaging said clevis with a respective one of said first and second pivot pins, each said intermediate portion angling away from said longitudinal axis in a first direction, and
each said distal portion angling back toward and past said longitudinal axis at an angle of between about 70 to 90 degrees relative thereto, wherein at least a portion of said distal portion extends along a horizontal axis perpendicular to said longitudinal axis beyond a longitudinal projection of said base portion in a second direction;
e) a rod extending at least partially through said hollow tube and having a first end and a second end, said rod being coupled to said first and second elongate opposed clamp members; and
f) actuating means engaged to said second end of said rod for imparting reciprocal motion to said rod relative to said hollow tube which reciprocal motion is translated into pivotal motion of said pivotally engaged opposed clamp members.

10. An endoscopic Jacobs type curved clamp apparatus according to claim 9, wherein:
said intermediate portion extends along said horizontal axis beyond said longitudinal projection of said base in a third direction opposite to said second direction.

11. An endoscopic Jacobs type curved clamp apparatus according to claim 10, wherein:
each said clamp member is an integral curvalinear element.

12. An endoscopic Jacobs type curved clamp apparatus according to claim 11, wherein:
each said clamp member traverses a distance of approximately 10 millimeters along said horizontal axis.

13. An endoscopic Jacobs type curved clamp apparatus according to claim 10, wherein:
each of said opposed clamp members has a clamping surface, and
each said clamping surface has grooves, wherein the grooves of said distal portions are at an angle of between about 0 to 20 degrees relative to said first longitudinal axis, and wherein the grooves of said intermediate portions are at an angle of between 70 to 90 degrees relative to said first longitudinal axis.

14. An endoscopic Jacobs type curved clamp apparatus according to claim 13, wherein:
each said clamp member is an integral curvalinear element, and
each said intermediate portion has a first length, and said base portions and said distal portions each have second and third lengths which are each about 0.25 to 0.5 the length of said first length.

15. An endoscopic Jacobs type curved clamp apparatus according to claim 10, wherein:
each said intermediate portion has a first length, and said base portions and said distal portions each have second and third lengths which are each about 0.25 to 0.5 the length of said first length.

* * * * *